United States Patent [19]
Beeler

[11] Patent Number: 5,161,842
[45] Date of Patent: Nov. 10, 1992

[54] DRUG SEARCH TOOL

[76] Inventor: Roxane M. Beeler, 137 Bardsdale Ave., Oxnard, Calif. 93035

[21] Appl. No.: 757,205

[22] Filed: Sep. 10, 1991

Related U.S. Application Data

[63] Continuation-in-part of Ser. No. 549,816, Jul. 9, 1990, abandoned.

[51] Int. Cl.$^5$ .............................................. B25J 11/00
[52] U.S. Cl. ....................................... 294/1.1; 294/55
[58] Field of Search ................... 294/1.1, 49, 51, 55, 294/59, 7; 73/426–429; 15/236.05; 30/324, 326, 327; D7/691

[56] References Cited

U.S. PATENT DOCUMENTS

| D. 166,444 | 4/1952 | Carre | 30/324 X |
|---|---|---|---|
| D. 239,907 | 5/1976 | Olsson | 73/426 X |
| D. 254,832 | 4/1980 | Zappa | D7/691 |
| D. 274,776 | 7/1984 | Molloy et al. | D7/691 |
| 1,011,613 | 12/1911 | Grasselly | 30/324 |
| 2,028,519 | 1/1936 | Peterkin et al. | 30/324 |
| 2,595,101 | 4/1952 | Russell | 73/426 |
| 3,001,404 | 9/1961 | McDonnell, Jr. et al. | 73/426 |

FOREIGN PATENT DOCUMENTS

| 703855 | 12/1941 | Fed. Rep. of Germany | 30/324 |
|---|---|---|---|
| 3724008 | 2/1989 | Fed. Rep. of Germany | 30/324 |

*Primary Examiner*—Margaret A. Focarino
*Assistant Examiner*—Dean J. Kramer
*Attorney, Agent, or Firm*—Robert M. Sperry

[57] ABSTRACT

A drug search tool which is designed to be passed through the crevices between furniture or vehicle seat cushions with ease, without the necessity of the police officer inserting his hand into such crevices, and which is formed with a recess that will serve to remove any articles located within such crevices, including hypodermic needles, without exposing the police officer to the risk of being stuck by such needles.

11 Claims, 1 Drawing Sheet

DRUG SEARCH TOOL

RELATED CASES

This application is a continuation-in-part of my co-pending patent application, Ser. No. 07/549,816, filed Jul. 9, 1990 and now abandoned.

BACKGROUND

1. Field of Invention

This invention relates to police enforcement tools and is particularly directed to tools for facilitating police in safely searching for illegal drugs and drug apparatus.

2. Prior Art

As is well known, drug interdiction has recently become a major activity of law enforcement organizations on federal, state and local levels. One of the most effective methods of accomplishing this is stopping and searching vehicles of suspected individuals. Unfortunately, this is an extremely hazardous operation. Aside from the fact that drug users and dealers are often armed and dangerous, when they are accosted by a police officer, they often try to hide the drugs and drug apparatus, such as hypodermic needles, in places where they believe the officer will not find them, for example, in crevices under or between furniture or vehicle seat cushions. Since the police are aware of this tendency, they try to search such areas by sliding their hand through such crevices. However, this exposes the police officer to a high risk of being stuck by such needles. This is especially dangerous, since it is well known that the hypodermic needles used by drug addicts are often shared by several users and are frequently contaminated. Furthermore, such shared hypodermic needles are known to be a leading source of AIDS infection and a police officer who gets stuck by such a needles runs a high risk of becoming infected by this disease. To reduce these risks, police officers often wear leather gloves, while making such a search. However, it is not uncommon for a hypodermic needle to penetrate through a glove. Consequently, the risk is still extremely high and no means has been proposed heretofore for reducing or overcoming this risk.

BRIEF SUMMARY AND OBJECTS OF INVENTION

These disadvantages of the prior art are overcome and a drug search tool is provided which facilitates searching the crevices between furniture or vehicle seat cushions, yet provides complete safety for the police officer making the search.

The advantages of the present invention are preferably attained by providing a drug search tool which is designed to be passed through the crevices between furniture or vehicle seat cushions with ease, without the necessity of the police officer inserting his hand into such crevices, and which is formed with a recess and a pouch, removably insertable into said recess, that will serve to remove any articles located within such crevices, including hypodermic needles, without exposing the police officer to the risk of being stuck by such needles.

Accordingly, it is an object of the present invention to provide improved means for protecting police officers against injury or infection while conducting searches for drugs and drug apparatus.

Another object of the present invention is to provide means for enabling a police officer to search the crevices between furniture or vehicle seat cushions without risk of injury or infection.

An additional object of the present invention is to provide means for enabling a police officer to locate and remove hypodermic needles and the like from obscure locations, such as the crevices between furniture or vehicle seat cushions, without risk of injury or infection by such needles.

A specific object of the present invention is to provide a drug search tool which is designed to be passed through the crevices between furniture or vehicle seat cushions with ease, without the necessity of the police officer inserting his hand into such crevices, and which is formed with a recess and a pouch, removably insertable into said recess, that will serve to remove any articles located within such crevices, including hypodermic needles, without exposing the police officer to the risk of being stuck by such needles.

These and other objects and features of the present invention will be apparent form the following detailed description, taken with reference to the figures of the accompanying drawing.

DETAILED DESCRIPTION OF THE INVENTION

Figure 1:
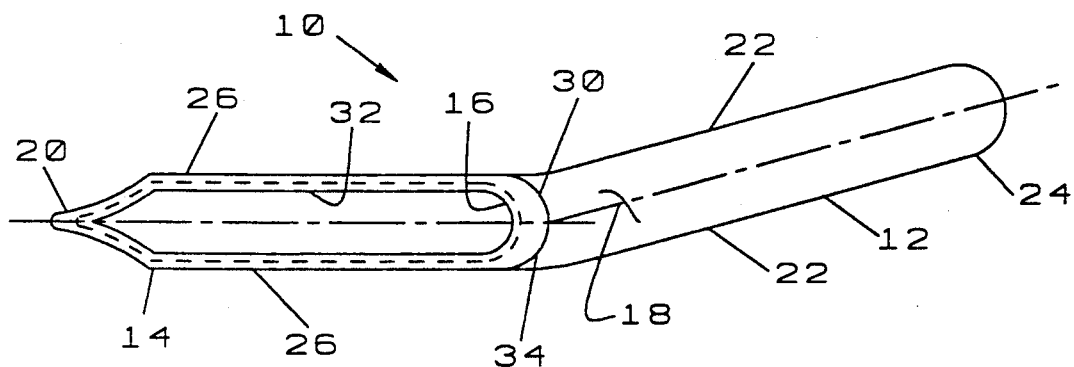
FIG. 1 is a top view of a drug search tool embodying the present invention.
Figure 2:
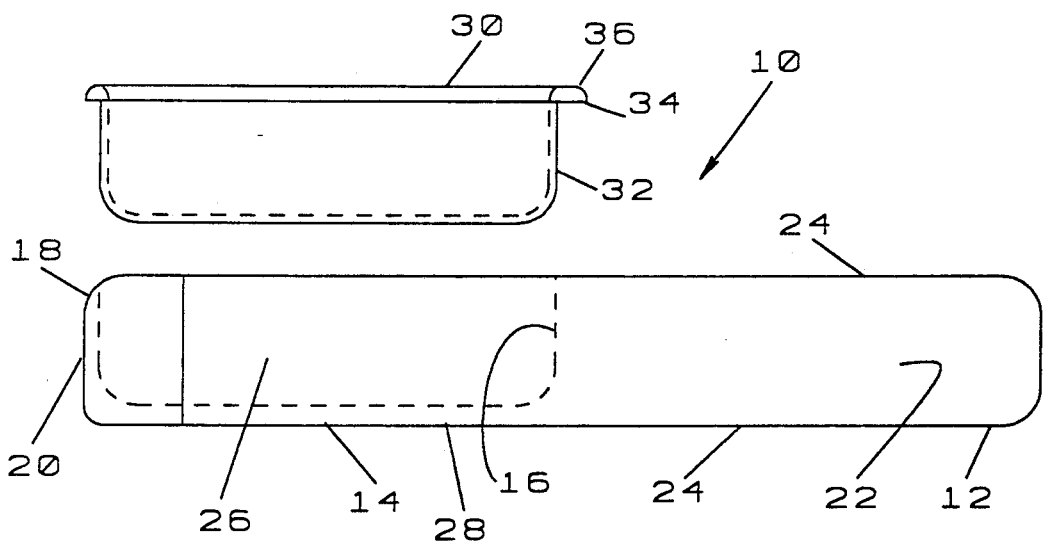
FIG. 2 is an exploded side view of the drug search tool of FIG. 1.
Figure 3:
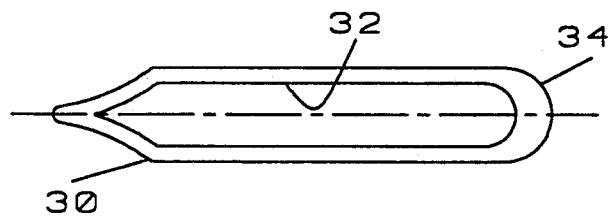
FIG. 3 is a top view of the insert for the drug search tool of FIG. 1.

In that form of the present invention chosen for purposes of illustration in the drawing, FIG. 1 shows a drug search tool, indicated generally at 10, comprising an elongated handle portion 12 and an article retrieving portion 14 formed with a recess 16 in one side 18 thereof and having a relatively pointed end 20. As shown, the handle portion 12 is formed to fit comfortably within the user's hand and has substantially parallel, flat upper and lower surfaces 22 with rounded sides 24. The handle portion 12 projects at an angle of approximately 30° from the article retrieving portion 14, which also has substantially parallel, flat upper and lower surfaces 26 and relatively vertical, rounded sides 28, with the recess 16 formed in one of the sides 28. A removable liner 30 is provided having a pouch portion 32 formed to slideably fit within the recess 16 of the article retrieving portion 14 and corresponding generally to the shape of the recess 16. The liner 32 has a flanged upper portion 34 formed to overlie the portion of the article retrieving portion 14 adjacent the recess 16 and to facilitate removal of the liner 30 from the recess 16 and, if desired, may have a tab 36 to further facilitate such removal. The tool 10 is formed of relatively rigid material, such as metal, plastic or wood. The liner 30 is disposable and may be made of similar, although lighter weight, material than that of the tool 10. Alternatively, the tool 10 may be made of disposable material, in which case, the liner 30 may be omitted.

In use, when a police officer desires to search the crevices between the cushions of furniture or vehicle seats, he grasps the drug search tool 10 by the handle portion 12 and inserts a liner 30, if used, into recess 16 of the tool 10. Then, he inserts the article retrieving portion 14 into the crevices between the furniture or vehicle seat cushions. The pointed end 20 of the article receiving portion 14 facilitates such insertion. Next, he sweeps the drug search tool 10 along the crevice with the open recess 16 facing in the direction of movement. Because of the rigidity of the drug search tool 10, the tool 10 will displace any solid articles, such as syringes, vials, etc. located within the crevice and will either catch such articles within the liner 30 or recess 16 or will force the articles out of the crevice so that they can be clearly seen. Moreover, any powdery substances, such as drugs, will be collected in the liner 30 or recess 16 of the drug search tool 10 and will be brought out of the crevice in the liner 30 or recess 16 when the tool 10 is withdrawn from the crevice. Thereafter, the liner 30 may be removed from the tool 10 and the liner 30 (or the entire tool 10, if no liner 30 is used) may be placed in an evidence bag, along with any articles which were displaced from the crevice by movement of the tool 10 through the crevice.

When such crevices are searched by sweeping the police officer's hand through the crevice, the only amounts of such powdery substances which will be retrieved will be the trace amounts which stick to the officer's hand. However, with the drug search tool 10, significant quantities of such powdery substances can be retrieved in the liner 30 or recess 16. Furthermore, if a hypodermic needle is located within the crevice, manual searching of the crevice will often result in the officer being impaled by the needle, whereas the drug search tool 10 will remove the hypodermic needle from the crevice without risk to the police officer.

Obviously, numerous variations and modifications can be made without departing from the spirit of the present invention. Therefore, it should be clearly understood that the form of the present invention described above and shown in the figures of the accompanying drawing are illustrative only and are not intended to limit the scope of the present invention.

What is claimed is:

1. A drug search tool comprising:
   a handle portion formed for convenient grasping and having substantially parallel upper and lower surfaces, and
   an article retrieving portion extending from said handle portion and having substantially parallel, flat upper and lower surfaces extending contiguous with the corresponding surfaces of said handle portion joined by relatively vertical sides with end portions located at the end of said article retrieving portion opposite from said handle portion which taper toward each other to form a pointed edge extending substantially parallel to the upper and lower surfaces to facilitate insertion of said tool between adjacent articles and having an opening formed in one of said vertical sides communicating with the interior of said tool.

2. The drug search tool of claim 1 wherein:
   said handle portion projects from said article retrieving portion at an angle of approximately 30°.

3. The drug search tool of claim 1 wherein:
   the sides of said article retrieving portion are substantially parallel.

4. The drug search tool of claim 1 wherein:
   said tool is formed of relatively rigid material.

5. The drug search tool of claim 1 wherein:
   said tool is formed of metal.

6. The drug search tool of claim 1 wherein:
   said tool is formed of plastic.

7. The drug search tool of claim 1 further comprising:
   a liner slideably insertable into said recess.

8. The drug search tool of claim 7 wherein:
   said liner has a pouch portion formed to fit slideably within said recess.

9. The drug search tool of claim 8 wherein:
   said liner has flange formed to overlie said article retrieving portion adjacent said recess.

10. A liner for use with a drug search tool having a handle portion formed for convenient grasping, an article retrieving portion extending from said handle portion and having substantially parallel, flat upper and lower surfaces joined by relatively vertical sides with a recess formed in one of said sides; said liner comprising:
    a pouch formed to be removably insertable into said recess and corresponding generally to the shape of said recess and having a tab to facilitate removal of said liner from said recess.

11. The liner of claim 10 wherein:
    said liner has a flange formed to overlie said article retrieving portion adjacent said recess.

* * * * *